(12) United States Patent
Majeed et al.

(10) Patent No.: US 11,865,203 B2
(45) Date of Patent: *Jan. 9, 2024

(54) SKIN CARE APPLICATIONS OF EXTRACELLULAR METABOLITES FROM BACILLUS COAGULANS

(71) Applicant: SAMI LABS LIMITED, Bangalore (IN)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US); Lakshmi Mundkur, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 114 days.

This patent is subject to a terminal disclaimer.

(21) Appl. No.: 17/324,698

(22) Filed: May 19, 2021

(65) Prior Publication Data

US 2021/0267880 A1 Sep. 2, 2021

Related U.S. Application Data

(62) Division of application No. 15/996,725, filed on Jun. 4, 2018, now abandoned.

(60) Provisional application No. 62/523,620, filed on Jun. 22, 2017, provisional application No. 62/516,090, filed on Jun. 6, 2017.

(51) Int. Cl.
*A61K 8/99* (2017.01)
*A61Q 17/04* (2006.01)
*A61Q 19/08* (2006.01)
*A61Q 19/00* (2006.01)

(52) U.S. Cl.
CPC .............. *A61K 8/99* (2013.01); *A61Q 17/04* (2013.01); *A61Q 19/00* (2013.01); *A61Q 19/08* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 6,461,607 B1 | 10/2002 | Farmer | |
| 7,807,185 B2 | 10/2010 | Farmer | |
| 9,579,352 B2 * | 2/2017 | Majeed | A61K 35/742 |
| 9,596,861 B2 * | 3/2017 | Majeed | A01N 37/12 |
| 10,966,919 B2 * | 4/2021 | Majeed | A61K 8/99 |
| 2015/0044317 A1 * | 2/2015 | Farmer | A61K 8/9728 424/780 |

OTHER PUBLICATIONS

Jan. 10, 2019 Office Action issued in U.S. Appl. No. 15/996,725.
Mar. 27, 2019 Office Action issued in U.S. Appl. No. 15/996,725.
Jan. 15, 2020 Office Action issued in U.S. Appl. No. 15/996,725.
Jan. 19, 2021 Office Action issued in U.S. Appl. No. 15/996,725.

* cited by examiner

*Primary Examiner* — Vera Afremova
(74) *Attorney, Agent, or Firm* — Oliff PLC

(57) ABSTRACT

Disclosed are the skin care applications of a composition containing the partially purified extracellular metabolite isolated from *Bacillus coagulans* MTCC 5856. More specifically, the invention discloses the ability of the partially purified extracellular metabolite isolated from *Bacillus coagulans* MTCC 5856 to confer protection to the skin fibroblasts against UV induced cell damage and apoptosis, oxidative stress and inflammation.

5 Claims, 4 Drawing Sheets
(2 of 4 Drawing Sheet(s) Filed in Color)

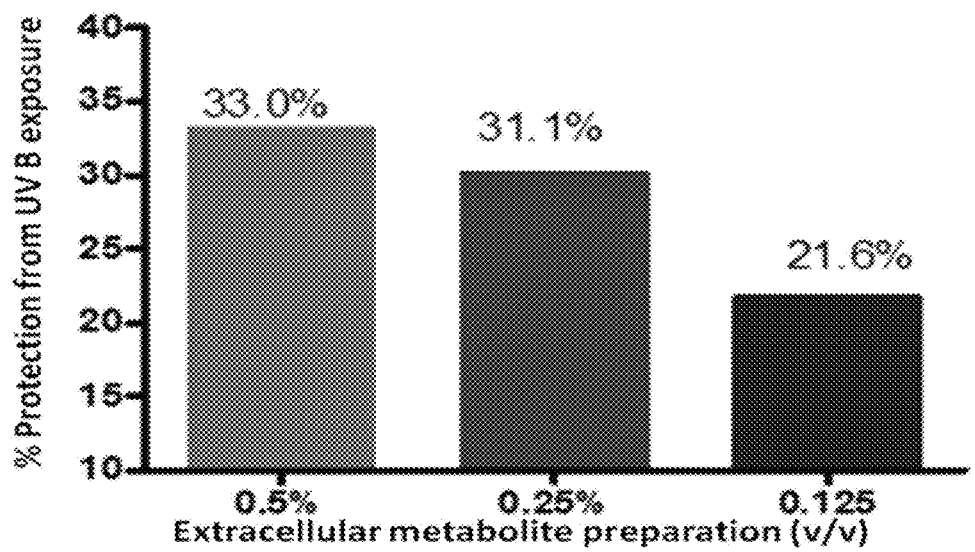
Fig. 2a
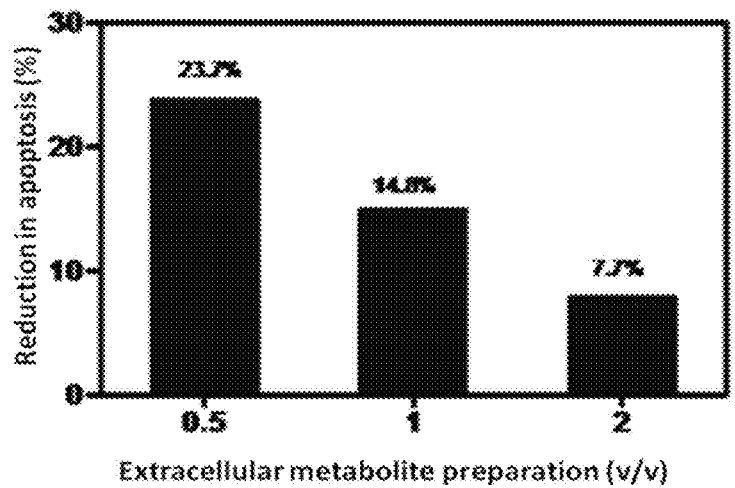

SKIN CARE APPLICATIONS OF EXTRACELLULAR METABOLITES FROM BACILLUS COAGULANS

CROSS-REFERENCE TO RELATED PATENT APPLICATIONS

This is a Division of application Ser. No. 15/996,725 filed Jun. 4, 2018, which in turn claims the benefit of U.S. Provisional Application No. 62/516,090 filed Jun. 6, 2017 and U.S. Provisional Application No. 62/523,620, filed Jun. 22, 2017. The disclosure of the prior applications is hereby incorporated by reference herein in its entirety.

BACKGROUND OF THE INVENTION

Field of the Invention

The invention in general relates to probiotics. More specifically, the present invention discloses the skin care applications of extracellular metabolite isolated from *Bacillus coagulans* MTCC 5856.

Description of Prior Art

The human skin is exposed to a wide range of environmental pollutants and harmful UV radiation, damaging the skin and leading to premature aging. Exposure to these harmful pollutants and UV radiation will increase the production of reactive oxygen species (ROS) and inflammatory markers, increasing the oxidative stress and inflammation in the skin cells thereby damaging the cellular biomolecules (lipids, sugars, proteins, and polynucleotides). Protection against these agents will eventually improve the skin texture and lead to graceful aging. The skin cells inherently possess cellular defense systems against ROS and inflammatory agents, which include nonenzymatic molecules (glutathione, vitamins A, C, and E, and several antioxidants present in foods) and enzymatic scavengers of ROS, with superoxide dismutase (SOD), catalase (CAT), and glutathione peroxidase (GPX). Apart from these, many natural molecules confer protection against the UV and ROS induced damage which are tapped commercially by different players in the cosmetic industry.

Probiotics are now garnering much attention in the skin care arena. Probiotic of the genera *Lactobacillus* and Bifidobacteria are reported for treatment of acne, rosacea, protection against aging, photo damage and UV:
1. Mary-Margaret Kober, Whitney P. Bowe, The effect of probiotics on immune regulation, acne, and photoaging, International Journal of Women's Dermatology, Volume 1, Issue 2, June 2015, Pages 85-89
2. Audrey Guéniche, David Philippe, Philippe Bastien, Stephanie Blum, Elif Buyukpamukcu, and Isabelle Castiel-Higounenc, Probiotics for photoprotection, Dermatoendocrinol, 2009 September-October; 1(5): 275-279

Probiotics strains alone or in combination with food have shown antioxidant activity and reduce damages caused by oxidation ((Yang Wang, Yapping Wu, Yuanyuan Wang, Han Xu, Xiaogiang Mei, Dongyou Yu, Yibing Wang and Weifen Li, Antioxidant Properties of Probiotic Bacteria, Nutrients, 2017 May; 9(5): 521). The extracelluar metabolities of probiotics are also reported to confer skin protection against microbial infections (U.S. Pat. No. 7,544,363B2). These products are now increasing being used in skin care applications (*Bacillus* Ferment, Ganeden Inc, https://cosmetics.specialchem.com/inci/bacillus-ferment, accessed 28 May 2018). However, it is well known in the scientific art that biological effects of probiotics or products thereof are strain specific and cannot be generalised among genera, species and strains (Probiotics: Depth/NCCIH, U.S. Department of Health and Human Services, National Institutes of Health). Hence, there exists a need to find a superior probiotic strain and its extracellular product that can be used effectively as a skin protection agent. The present invention solves the above mentioned problem by disclosing the beneficial effects of partially purified extracellular metabolite preparation of *Bacillus coagulans* for skin protection/care.

It is the principle objective of the invention to disclose the use of a composition containing partially purified extracellular metabolite preparation of *Bacillus coagulans* MTCC 5856 as a skin care agent by conferring protection against UV radiation and UV induced DNA damage.

It is another objective of the invention to disclose the use of a composition containing partially purified extracellular metabolite preparation of *Bacillus coagulans* MTCC 5856 as an anti-oxidant and anti-inflammatory agent.

The present invention fulfills the above mentioned objectives and provides further related advantages.

Deposit of Biological Material

The deposit of biological material *Bacillus coagulans* bearing accession number MTCC 5856, mentioned in the instant application has been made on 19 Sep. 2013 at Microbial Type Culture Collection & Gene Bank (MTCC), CSIR-Institute of Microbial Technology, Sector 39-A, Chandigarh-160036, India.

SUMMARY OF THE INVENTION

The present invention discloses the skin care applications of a composition containing the partially purified extracellular metabolite isolated from *Bacillus coagulans* MTCC 5856. More specifically, the invention discloses the ability of the extracellular metabolite isolated from *Bacillus coagulans* MTCC 5856 to confer protection to the skin fibroblasts against UV induced cell damage and apoptosis, oxidative stress and inflammation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1c is the graphical representation showing the % protection against UV B exposure by the partially purified extracellular metabolite preparation from *Bacillus coagulans* MTCC 5856

FIG. 2a is the graphical representation showing the % reduction in apoptotic cells by the partially purified extracellular metabolite preparation from *Bacillus coagulans* MTCC 5856

DESCRIPTION OF THE MOST PREFERRED EMBODIMENTS

Figure 1A:
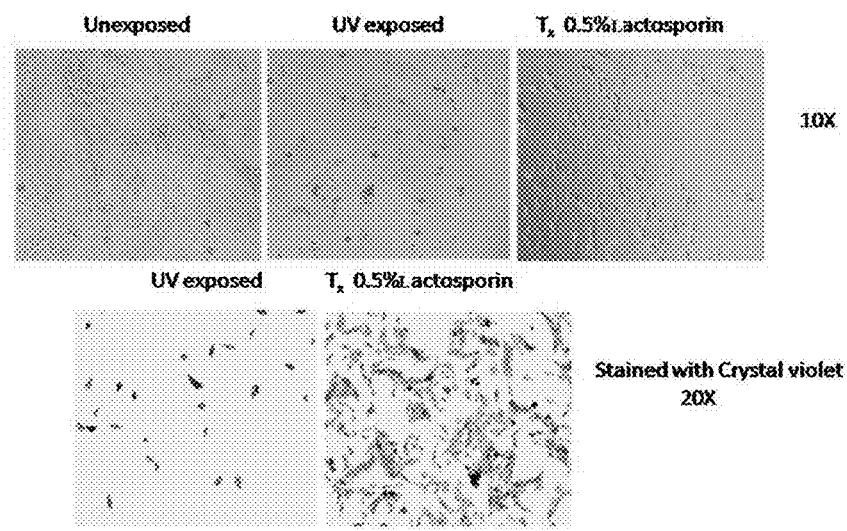
FIG. 1a shows fibroblast cells stained with crystal violet incubated with different concentration of the partially purified extracellular metabolite preparation from *Bacillus coagulans* MTCC 5856, conferring UV protection.

In the most preferred embodiment, the present invention discloses a method of protecting skin fibroblasts from UV induced damage, said method comprising steps of brining into contact skin fibroblast cells with effective concentration of a composition containing partially purified extracellular metabolite preparation from *Bacillus coagulans*, to bring about the effect of protection against UV-A and UV-B induced cell damage and apoptosis. In a related embodiment, the strain of *Bacillus coagulans* is *Bacillus coagulans* MTCC 5856. In yet another related embodiment, effective concentration of the partially purified extracellular metabolite preparation is 0.01% v/v to 2.0% v/v of the total composition.

In another aspect, the invention discloses a composition containing partially purified extracellular metabolite preparation from *Bacillus coagulans* for use as a skin care agent, wherein the composition confers skin protection by a) protecting the skin against UV-A and UV-B induced cell damage and apoptosis, b) reducing oxidative stress in the skin by scavenging ROS and c) reducing inflammation by decreasing the levels inflammatory markers in the skin. In a related embodiment, the strain of *Bacillus coagulans* is *Bacillus coagulans* MTCC 5856. In yet another related embodiment, effective concentration of the partially purified extracellular metabolite preparation is 0.01% v/v to 2.0% v/v of the total composition. In yet another related embodiment the composition is formulated with pharmaceutically/cosmeceutically acceptable excipients, adjuvants, bases, diluents, carriers, conditioning agents, bioavailability enhancers, antioxidants and preservatives and/or incorporated into formulations containing skin care ingredients and administered topically in the form of creams, gels, lotions, powder, serum, oil, suspensions, ointments, soaps, scrubs, emulsions, and compacts.

In another preferred embodiment, the invention discloses a composition containing partially purified extracellular metabolite isolated from *Bacillus coagulans* for use as an anti-oxidant and anti-inflammatory agent. In another related embodiment, the strain of *Bacillus coagulans* is *Bacillus coagulans* MTCC 5856. In yet another related embodiment the composition is formulated with pharmaceutically/cosmeceutically acceptable excipients, adjuvants, bases, diluents, carriers, conditioning agents, bioavailability enhancers, and preservatives and/or incorporated into formulations containing skin care ingredients and administered topically in the form of creams, gels, lotions, powder, serum, oil, suspensions, ointments, soaps, scrubs, emulsions, and compacts.

Specific illustrative examples enunciating the most preferred embodiments are included herein below.

Example 1: Protection Against UV Radiation

Isolation of Extracellular Metabolite

The extracellular metabolite from *Bacillus coagulans* MTCC 5856 was isolated as per the steps outlined in U.S. Pat. No. 9,596,861, the disclosure of which is incorporated herein by reference. The method comprises the steps of:

1. Inoculating a culture of *Bacillus coagulans* MTCC 5856 exhibiting 99% genetic homology with the known bacterial strains *Bacillus coagulans* ATCC 31284, *Bacillus coagulans* NBRC 3887 and *Bacillus coagulans* ATCC 7050 into 1.0 liter of Glucose Yeast Extract Acetate broth medium (HiMedia, Mumbai India) or MRS broth containing 0.5% tween 80 or Corn steep powder media;
2. Allowing the fermentation in the inoculated medium of step 1 to proceed for 24-48 h at 37° C. with 120 rpm;
3. Centrifuging the fermentation broth of step 2 at 4000-7000 rpm;
4. Concentrating supernatants 10 fold by using rotary evaporator at 50° C. of step 3.
5. Adding 150 ml of chilled acetone drop by drop to 100 ml of tenfold concentrated supernatants of step 4, followed by mixing;
6. Incubating the mixture of step 5 at 0° C. for 30 minutes followed by centrifuging at 7000-8000 rpm;
7. Discarding the pellet obtained in step 6 and collecting 60% acetone saturated supernatant (~200 ml).
8. Concentrating the acetone saturated supernatant in step 7 to 50 ml by rotary evaporator.
9. Adjusting the pH to 5.0 by using 4N HCl, filtered (0.22 micron; Millex, Millipore, India) and stored at −20° C. till further use.
10. Freeze drying/spray drying/tray drying the supernatant of step 8.

The product is commercially available under the tradename LACTOSPORIN® INCI: *Bacillus* ferment filtrate extract) from Sabinsa Corporation, USA.

Materials and Methods

The amount of UVA radiation on earth's surface is approximately 20-fold higher than that of UVB. It is responsible for the tanning effects of human skin and had been considered mostly harmless for many years. UV radiation has broad spectrum, ranging from 40 to 400 nm (30-3 eV), which is divided into Vacuum UV (40-190 nm), Far UV (190-220 nm), UVC (220-290 nm), UVB (290-320), and UVA (320-400 nm), of which the latter two are medically important. There are two distinct subtypes of UVA radiation. Short-wave UVA (320-340 nm) and long-wave UVA (340-400 nm), constitute most of UVA radiation. The amount of exposure to UVA usually remains constant, whereas UVB exposure occurs more hi the summer UV radiations are responsible for high incidence of premature skin aging, referred to as photoaging, as well as skin cancer and melanoma. UVB irradiation has been demonstrated to produce ROS in the cells and skin, which induces the synthesis of matrix metalloproteinase (MMPs), causing photoaging effects in skin. The effects of UVA manliest usually after a long duration of exposure, even if doses are low. It has been postulated that UVA up regulates the formation of matrix metalloproteinase (MMPs), enzymes that degrade the matrix protein's elastin and collagen, which, if not prevented, can result in marked reduction in skin elasticity and increased wrinkling UVA can penetrate deeper into the skin in comparison to UVB and contributes to photoaging, photocarcinogenesis and photodermatosis and increase in reactive oxygen species (ROS) in fibroblasts and cells which are deeper inside the skin.

Materials

Cells: Human dermal fibroblasts (HDFa)-cells were purchased from ThermoFisher Scientific/Mouse fibroblast cell line (Balb/C 3T3) purchased from National centre of cell collection (NCOS, Pune, India) and maintained as a monolayer culture in Dulbeccos modified minimal essential medium (DMEM) Life technologies, CA, USA) supplemented with 10% (v/v) heat-inactivated foetal bovine serum (FBS; GIBCO/Invitrogen, Carlsbad, Calif.), 100 units/mL penicillin and 100 µg/mL streptomycin (Life technologies) at 37° C. in a humidified 5% $CO_2$ incubator. HDFa cells were maintained in Fibroblast media from Thermo Fisher.

Reagents: Dulbeccos modified minimal essential medium (DMEM), Fetal bovine serum (FBS), Crystal violet, Neutral red dye Instrument: Microscopes-Phase contrast (Olympus, Japan) and Steromicroscope (Leica, Germany), Microplate reader (Tecan)

Procedure

Neutral Red is a weak cationic dye that readily penetrates cell membranes by non-diffusion, accumulating intracellularly in lysosomes. Alterations of the cell surface of the sensitive lysosomal membrane brought about by the action of xenobiotics result in a decreased uptake and binding of NR. It is thus possible to distinguish between viable, damaged or dead cell. Cytotoxicity in this test is expressed as a concentration-dependent reduction of the uptake of the vital dye Neutral Red when measured 24 hours after treatment with the test chemical and irradiation. Exposure to UVA or UVB causes cell death which can also be visualized by imaging under high resolution phase contrast microscope. The viable cells are then stained using crystal violet which stains the nuclei. The cells are imaged in a bright field microscope to visualize the live cells.

Cells were maintained in culture for 24 h for formation of monolayers. Balb/c cells were seeded at a density of $1\times10^4$ cells/well in 96 well plates. Cells were allowed to adhere and form a monolayer for 24 hours. Cells were pretreated with varying non toxic concentrations of the extracellular metabolite from *Bacillus coagulans* in PBS for 60 minutes in three individual plates. One plate was exposed to UVA intensity of 15 Joules/m² for 60 mins, the second plate was exposed to UV-B intensity of 4.6 Joule/m² for 30 mins and the third plate was kept in dark. Cells were washed with sterile buffer and fresh culture medium (5% of FBS) with respective concentrations of extracellular metabolite from *Bacillus coagulans* was added followed by incubation for 24 hours at 37° C. in a $CO_2$ incubator. Neutral Red (50 pg/mL) (3-amino-7-dimethylamino-2-methylphenazine hydrochloride), was added to the cells for 3 hours. The uptake of NR by the cells was determined by lysing the cells and reading the absorbance at 540 nm in a spectrophotometer.

Cells were observed under phase contrast microscope. They were stained using 0.5% crystal violet in 20% methanol for 20 minutes and images were recorded.

Results

Figure 1B:
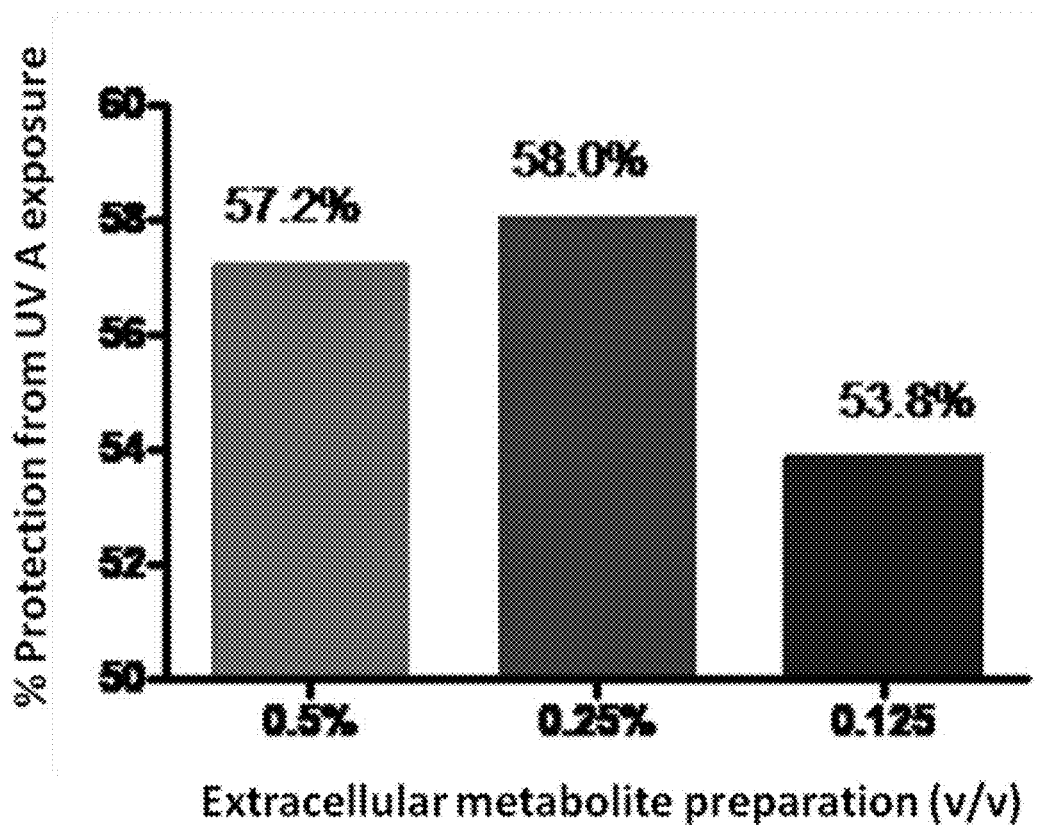
FIG. 1b is the graphical representation showing the % protection against UV A exposure by the partially purified extracellular metabolite preparation from *Bacillus coagulans* MTCC 5856

The results indicated that the extracellular metabolite has the potential to protect fibroblast cells from UVA and UVB induced toxicity (FIGS. 1a, 1b, and 1c) and has potent use and benefits as a UV protective agent in cosmetic applications.

Example 2: Protection Against UV Induced DNA Damage

Isolation of Extracellular Metabolite

The extracellular metabolite from *Bacillus coagulans* MTCC 5856 was isolated as per the steps outlined in U.S. Pat. No. 9,596,861. The product is commercially available under the tradename LACTOSPORIN® (INCI: *Bacillus* ferment filtrate extract) from Sabinsa Corporation, USA.

Materials and Methods

UV light can accelerate premature ageing and DNA damage. UVB-induced apoptosis is the programmed cell death of cells that become damaged by ultraviolet rays. Apoptosis is a physiological process that promotes cell death which can be termed as active suicide of cells. Failure of the body to remove DNA damaged cells increases the risk of skin cancer. Reduction in apoptosis and cell death is hallmark of anti ageing molecule.

Materials

Cells: Skin cells (dermal fibroblasts, keratinocytes or melanocytes) purchased from American Type Culture Collection (ATCC, Manassas, Va.) and maintained as a monolayer culture in Dulbeccos modified minimal essential medium (DMEM) Life technologies, CA, USA) supplemented with 10% (v/v) heat-inactivated foetal bovine serum (FBS; GIBCO/Invitrogen, Carlsbad, Calif.), 100 units/mL penicillin and 100 µg/mL streptomycin (Life technologies) at 37° C. in a humidified 5% $CO_2$ incubator.

Reagents: Annexin-FITC, Propidium Iodide-Apoptosis detection kit, Biovision, USA DMEM, FBS phosphate buffer (pH7.4)

Instrument: Flow cytometry (BD-FACS-CantoH)

Procedure

Exposure of skin cells to UVB light (290-320 nm) triggers cell death and fragmentation of DNA (apoptosis). The cells which are undergoing apoptotic death can be specifically stained using an antibody to a protein called Annexin. In normal cells, phosphatidylserines (PS, membrane phospholipids) are held on the inner layer of the cell membrane, so Annexin V does not attach to the cells. During early apoptosis, the PS are exposed on the outer layer, where they attach to the FITC-labelled Annexin V and stain the cell surface green. During late apoptosis, propidium iodide (PI) enters the cell and stains the contents red.

Figure 2B:
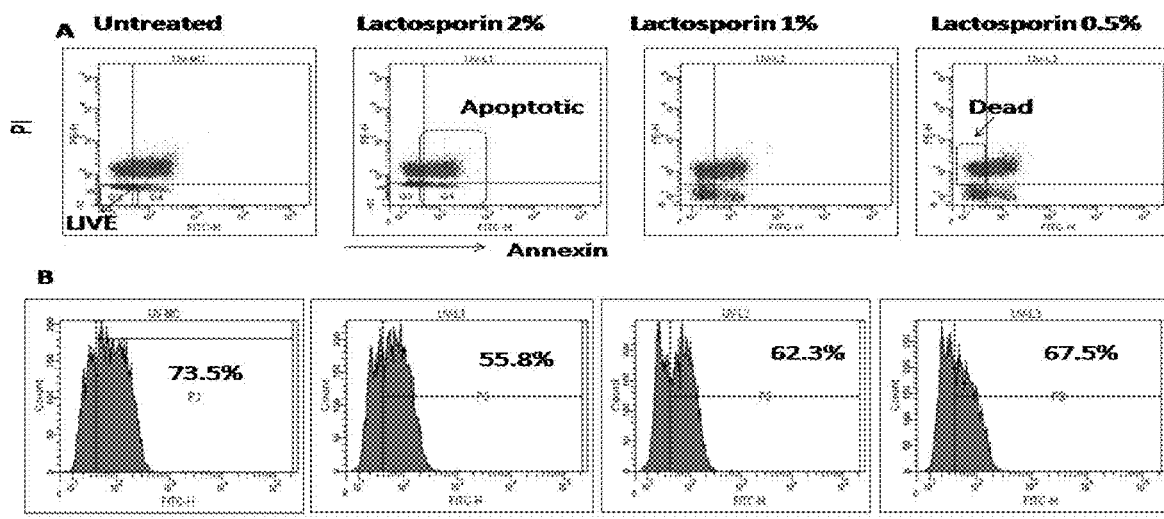
FIG. 2b shows dot plot of UV-B exposed cells treated with different concentration of partially purified extracellular metabolite preparation from *Bacillus coagulans* MTCC 5856 (A) and its histogram (B)

Cells ($2\times10^5$) were treated with different concentrations of extracellular metabolite from *Bacillus coagulans* for 24 hours. Cells were exposed to UVB rays for 30 min and labelled with Annexin-FITC and propidium iodide (PE). Annexins are a family of calcium-dependent phospholipid-binding proteins, which bind to phosphatidylserine (PS) to identify apoptotic cells. The cells were analysed by flow cytometry to determine the cell death and the apoptotic cells Results The extracellular metabolite from *Bacillus coagulans* was found to reduce apoptotic cell death induced by UVB radiation. Cell damage was reduced by 23.7% at a concentration of 0.5%. (FIGS. 2a and 2b).

Example 3: Reduction in Oxidative Stress Induced by UV Radiation

Isolation of Extracellular Metabolite

The extracellular metabolite from *Bacillus coagulans* MTCC 5856 was isolated as per the steps outlined in U.S. Pat. No. 9,596,861. The product is commercially available under the tradename LACTOSPORIN® (INCI: *Bacillus* ferment filtrate extract) from Sabinsa Corporation, USA.

Materials and Methods

Skin cells are constantly exposed to reactive oxygen species (ROS) and oxidative stress from exogenous and endogenous sources. UV radiation is the most important environmental factor in the development of skin cancer and skin aging. Oxidative stress is developed in skin when the UV-induced generation of ROS exceeds the ability of endogenous defence mechanism. The reduction of oxidative stress can be achieved either by lowering exposure to UVR and/or by increasing levels of antioxidant defence mechanism. Melanin present in the skin and the anti oxidant enzymatic reactions protect our skin from oxidative stress. Many studies have shown treatment with antioxidants prior to UV exposure can prevent oxidative damage to cellular biomolecules.

Materials

Cells: Human dermal fibroblasts (HDFa)-cells were purchased from ThermoFisher Scientific/Mouse fibroblast cell line (Balb/C 3T3) purchased from National centre of cell collection (NCCS, Pune, India). Cells were maintained in fibroblast media (Gibco) at 37° C. in a humidified 5% $CO_2$ incubator.

Reagents: Fibroblast media (Gibco) DCFH-DA Instrument: FluoStar Optima microplate reader Procedure Reactive oxygen species include a number of molecules that damage DNA and RNA and oxidize proteins and lipids (lipid peroxydation). These reactive molecules contain an oxygen atom/molecule and include $H_2O_2$ (hydrogen peroxide), NO (nitric oxide), $O_2^-$ (oxide anion), peroxynitrite ($ONOO^-$), hydrochlorous acid (HOCl), and hydroxyl radical ($OH^-$).

5-(and 6)-chloromethyl-20,70-dichlorohydrofluorescein diacetate (CM-H2DCFDA) freely permeates the plasma membrane and is hydrolyzed in the cytosol to form the DCFH carboxylate anion. Oxidation results in the formation of fluorescent DCF, which is maximally excited at 495 nm and emits at 520 nm.

Figure 3:
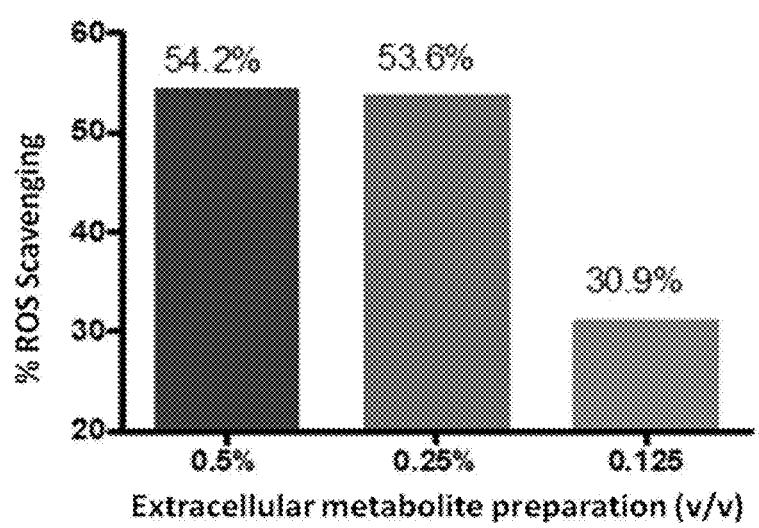
FIG. 3 is the graphical representation showing the % ROS scavenging by the partially purified extracellular metabolite preparation from *Bacillus coagulans* MTCC 5856

Fibroblast cells were seeded at 50,000 cells per well in 96 well black plates and allowed to grow as a monolayer for 24 hours. Cells were pretreated with different concentration of extracellular metabolite for one hour. The plate was exposed to UVA radiation for 1 hour. Freshly prepared DCFH-DA reagent was added to all the wells (2 ug/well). The plate was incubated at 37° C. for 30 mins. Fluorescence was recorded at 485:520, Ex:Em wavelength in FluoStar Optima microplate reader Results The extracellular metabolite preparation from *Bacillus coagulans* MTCC 5856 showed dose dependent reduction in ROS induced by UV exposure in fibroblasts. (FIG. 3).

Example 4: Anti Oxidant Activity of Extracellular Metabolite Preparation from *Bacillus coagulans* MTCC 5856

Isolation of Extracellular Metabolite

The extracellular metabolite from *Bacillus coagulans* MTCC 5856 was isolated as per the steps outlined in U.S. Pat. No. 9,596,861. The product is commercially available under the tradename LACTOSPORIN® (INCI: *Bacillus* ferment filtrate extract) from Sabinsa Corporation, USA.

DPPH-Free Radical Scavenging Assay

Reactive oxygen species (ROS) including superoxide, hydroxyl, peroxyl, and alkoxy radicals are produced by normal metabolic processes. Under normal condition, these free radicals are scavenged by the cellular anti oxidants and remain in equilibrium. Radiations, toxins and pollutants increase the ROS which can induce oxidative damage to biomolecules such as lipids, nucleic acids, proteins and carbohydrates. These ROS induced damage causes skin irritation, inflammation, ageing, cancer and many other diseases, α,α-diphenyl-β-picrylhydrazyl (DPPH) free radical scavenging method is one of the first approach for evaluating the antioxidant potential of a compound.

Materials

Equipment: Tecan microplate reader (TECAN Ltd, Männedorf, Switzerland) Reagents: 0.1 mM of DPPH in ethanol, 0.1 M phosphate buffered saline (pH7.4) Microtitre plates: 96 well microtitre plates (Corning, USA)

Procedure

DPPH is a stable free radical in a methanolic solution with an absorbance at 520 nm. If the free radicals are scavenged by an anti oxidant molecule, the resulting solution appears yellow. The hydrogen atoms or electrons donation ability of the extracellular metabolite was measured by the bleaching of purple coloured DPPH methanol solution.

The extracellular metabolite preparation was diluted in PBS. For the DPPH radical scavenging assay, 20 μL of extracellular metabolite preparation was mixed with 180 μL of DPPH in methanol in a 96 well plate following the method as described earlier (Clarke et al., 2013). The plate was kept in the dark for 15 min, after which the absorbance of the solution was measured at 540 nm using a microplate reader (TECAN Ltd, Männedorf, Switzerland). Blanks (DMSO, methanol) and standard (Trolox solution in DMSO) were recorded simultaneously. The extracts were screened with variable concentrations to establish the inhibition concentration ($IC_{50}$, the concentration reducing DPPH absorbance by 50%).

The free radical scavenging activity was calculated as follows, $$\% \text{ scavenging activity} = \frac{(B-C)-(S-C)}{(B-C)} \times 100$$

Figure 4:
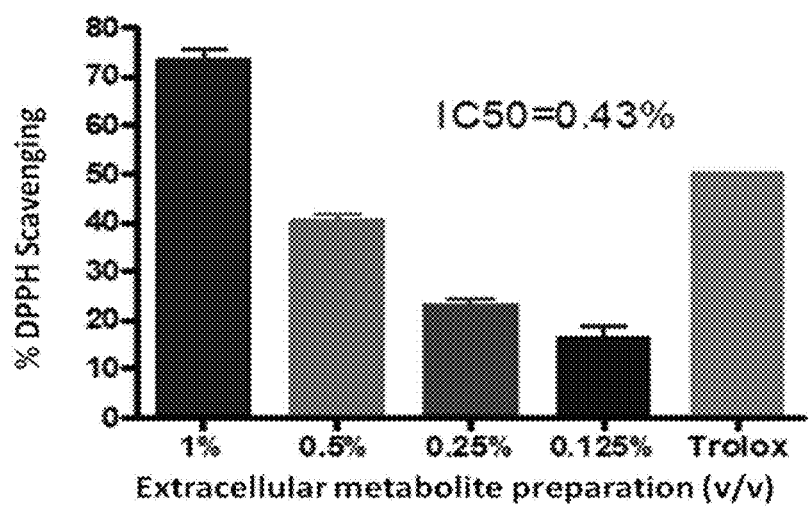
FIG. 4 is the graphical representation showing the % DPPM scavenging by the partially purified extracellular metabolite preparation from *Bacillus coagulans* MTCC 5856.

Where,
B=Absorbance of reference solution (OD of DPPH)
C=Absorbance of reference solution blank (OD of Methanol only)
S=Absorbance of test solution
C=Absorbance of test solution blank Results The extracellular metabolite preparation showed dose dependent anti oxidant activity comparable to Trolox®. The concentration at which 50% of enzyme activity in inhibited ($IC_{50}$) was found to be 0.43% for the extracellular metabolite preparation. (FIG. 4)

Example 5: Anti Inflammatory Activity of Extracellular Metabolite Preparation from *Bacillus coagulans* MTCC 5856

Isolation of Extracellular Metabolite

The extracellular metabolite from *Bacillus coagulans* MTCC 5856 was isolated as per the steps outlined in U.S. Pat. No. 9,596,861. The product is commercially available under the tradename LACTOSPORIN® (INCI: *Bacillus* ferment filtrate extract) from Sabinsa Corporation, USA.

Materials and Methods

Skin inflammation can result from exposure to UV or ionizing radiation, allergens, or by contact with chemical irritants or allergens. When the skin is exposed to an inflammatory agent, the cells in the skin produce an inflammatory messenger known as cytokine. These cytokines trigger an inflammatory cascade which produce other cytokines activate the blood cells, produce free radicals which damage the skin.

Materials

Cells: THP1-human monocytes purchased from American Type Culture Collection (ATCC, Manassas, Va.) and maintained as a monolayer culture in Rosewell park memorial institute Medium (RPMI Life technologies, CA, USA) supplemented with 10% (v/v) heat-inactivated foetal bovine serum (FBS; GIBCO/Invitrogen, Carlsbad, Calif.), 100 units/mL penicillin and 100 µg/mL streptomycin (Life technologies) at 37° C. in a humidified 5% $CO_2$ incubator.

Reagents and buffers: Lipopolysaccharide (LPS, Sigma chemicals, USA), Phosphate buffered saline, RPMI, FBS ELISA kit: Human TNF ELISA kit, Krishgen Biosciences, USA Procedure Anti inflammatory activity was examined using human monocyte/macrophage cell line THP-1. Monocytes respond to lipopolysaccharides (LPS) by secreting proinflammatory cytokines. Tumour necrosis factor (TNF-α) is one of the principle cytokine which triggers a cascade of inflammatory reactions. The concentration of TNF-α was measured using an Enzyme linked Immunosorbent assay (ELISA). Reduction in TNF-α concentration indicates an anti inflammatory activity of the compound.

$1 \times 10^5$ THP-1 cells were stimulated with 100 ng with lipopolysacharide (LPS, 0.1 µg/mL) to induce TNF-α secretion. Cells were pre treated with different concentrations extracellular metabolite preparation before LPS treatment. The cell supernatants were collected 24 hour after treatment and secreted TNF-α as estimated by cytokine ELISA as described by the manufacturer. Unstimulated cells were used as negative control. The limit of detection was <1 pg/mL.

Results

The results indicated the extracellular metabolite preparation significantly inhibited TNF-α (Table 1), indicating significant anti inflammatory activity without affecting the cell viability.

TABLE 1

Anti Inflammatory activity of the extracellular metabolite preparation from *Bacillus coagulans*

| Extracellular metabolite Conc. (v/v) | % Inhibition | Cell viability |
| --- | --- | --- |
| 2% | 86.71 | 100% |
| 1% | 86.84 | 100% |
| 0.50% | 89.87 | 100% |

Example 6: Formulations Containing Extracellular Metabolite Preparation from *Bacillus coagulans* for Skin Care The composition containing the extracellular metabolite from *Bacillus coagulans* MTCC 5856 may be formulated with pharmaceutically/cosmeceutically acceptable excipients, adjuvants, bases, diluents, carriers, conditioning agents, bioavailability enhancers, antioxidants and preservatives and/or incorporated into formulations containing anti-aging ingredients and administered topically in the form of creams, gels, lotions, powder, serum, oil, suspensions, ointments, soaps, scrubs, emulsions, and compacts.

In a related aspect, one or more skin care ingredients are selected from the group consisting of, but not limited to, Alpha Lipoic Acid, oxyresveratrol, Beet root extract, *Boswellia serrata* Extract, β boswellic acids, *Boswellia serrata* oil, *Centella asiatica* Extract, triterpenes, *Garcinia indica* extract, anthocyanins, *Cocos nucifera* extract and juice, *Coleus forskohlii* Extract, forskolin, *Coleus forskohlii* Oil, Tetrahydropiperine, Eliagic Acid, Gallnut Extract, polyphenols, Galanga Extract, Glycyrrhizinic Acid, Green Tea Extract, Epigallocatechin Gallate, Licorice extract, Mono-Ammonium Glycyrrhizinate, Limonoids, Oleanolic Acid, Cosmetic peptides (Oleanolic acid linked to Lys-Thr-Thr-Lys-Ser, Oleanolic acid linked to Lys-Val-Lys), Oleuropein, Piper longumine extract, piperine, Eliagic acid, Pomegranate Extract (Water Soluble), pterostilbene, resveratrol, *Pterocarpus santalinus* extract, Rosemary Extract, Rosmarinic Acid, Amla extract, beta glucogallin, tetrahydrocurcumin, *Salvia Officinalis* (Sage) Leaf Extract, Ursolic Acids, Saponins, *Sesamum indicum* (Sesame) Seed Extract, Sesamin and sesamolin, moringa oil, moringa seed extract, Horse Chestnut Extract, Vitex Oil, Xymenynic Acid, ethyl ascorbic acid, Argan oil, Lemon peel extract, turmeric oil, Barley Beta Glucans, coenzyme Q10, olive oil, avocado oil and cranberry oil.

In another related aspect, one or more anti-oxidants and anti-inflammatory agents are selected from the group consisting of, but not limited to, vitamin A, D, E, K, C, B complex, rosmarinic acid, Alpha Lipoic Acid, oxyresveratrol, Eliagic Acid, Glycyrrhizinic Acid, Epigallocatechin Gallate, plant polyphenols, Giabridin, moringa oil, oleanolic acid, Oleuropein, Carnosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosyl-rutin, calalase and the superoxide dismutase, glutathione, selenium compounds, butylated hydroxyanisole (BHA), butylated hydroxytoluene (BHT), sodium metabisulfite (SMB), propyl gallate (PG) and amino acid cysteine.

In another related aspect, one or more bioavailability enhancers are selected from the group, but not limited to, piperine, tetrahydropiperine, quercetin, Garlic extract, ginger extract, and naringin.

Tables 2-6 provide illustrative examples of skin care formulations containing partially purified extracellular metabolite preparation from *Bacillus coagulans* MTCC 5856 (*Bacillus* ferment filtrate extract)

TABLE 2

Skin Care Lotion

Active Ingredients

*Bacillus* ferment filtrate extract 0.01%-2%
Tetrahydrocurcumin, licorice extract, Pterostilbene, Tetrahydropiperine,
Galanga extract, Niacinamide TABLE 2-continued

| Skin Care Lotion |
|---|
| Other ingredients/Excipients |
| Chelating agents, Humectants, Emollients, Emulsifiers, Antioxidants, Preservatives, Thickeners (Like Cellulose derivatives, Acrylates Crosspolymer, Acrylates/C10-30 Alkyl Acrylate Cross Polymer, Carbomers), Neutralising agents, Fragrance, Silicones. |

TABLE 3

| Skin care Hydration Cream |
|---|
| Active Ingredients |
| *Bacillus* ferment filtrate extract 0.01%-2% Amaranthus extract, Niacinamide, Vitamin E, Shea butter, Olive oil, D-Panthenol |
| Other ingredients/Excipients |
| Bioavailability enhancers (Piperine extract or Tetrahydropiperine (Cosmoperine ®)), Fragrance, Thickeners (Cellulose derivatives or Acrylates Cross Polymer), Chelating agents, Humectants, Emollients, Emulsifiers, Antioxidants, Preservatives, Neutralising agents, and Silicones. |

TABLE 4

| Sunscreen cream |
|---|
| Active Ingredients |
| *Bacillus* ferment filtrate extract 0.01%-2% Galanga extract, Vitamin E acetate |
| Other ingredients/Excipients |
| Chelating agents, Sunscreen agents (Physical & Chemical), Humectants, Emollients, Emulsifiers, Antioxidants, Preservatives, Thickeners (Like Cellulose derivatives, Acrylates Crosspolymer, Acrylates/C10-30 Alkyl Acrylate Cross Polymer, Carbomers), Neutralising agents, Fragrance, Silicones. |

TABLE 5

| Cleanser |
|---|
| Active Ingredients |
| *Bacillus* ferment filtrate extract 0.01%-2% Tetrahydrocurcumin, licorice extract, Pterostilbene, Tetrahydropiperine, Lemon peel extract, papaya extract |
| Other ingredients/Excipients |
| Chelating agents, Surfactants (Anionic, Cationic, Cationic, Amphoteric), Fruit Extracts, Bioavailabilty enhancers, Humectants, Emollients, Emulsifiers, Antioxidants, Preservatives, Thickeners (Like Cellulose derivatives, Acrylates Crosspolymer, Acrylates/C10-30 Alkyl Acrylate Cross Polymer, Carbomers), Neutralising agents, Fragrance. |

TABLE 6

| Face Scrub |
|---|
| Active Ingredients |
| *Bacillus* ferment filtrate extract 0.01%-2% Cocus nucifera extract, walnut scrub, neem oil, Niacinamide, lemon peel extract, Vitamin E acetate |
| Other ingredients/Excipients |
| Chelating agents, Surfactants (Non Ionic Surfactants), Humectants, Emollients, Emulsifiers, Antioxidants, Preservatives, Thickeners (Like Cellulose derivatives, Acrylates Crosspolymer, Acrylates/C10-30 Alkyl Acrylate Cross |

TABLE 6-continued

Face Scrub

Polymer, Carbomers), Neutralising agents, Fragrance, Coloring agents as per F D&C, bioavailability enhancers (Piperine extract or Tetrahydropiperine (Cosmoperine ®)).

The above formulations are merely illustrative examples; any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing, from the spirit and scope of the invention. The scope of the invention is to be interpreted only in conjunction with the appended claims.

We claim:

1. A method of therapeutic management of UV induced damage in a subject's skin, said method comprising contacting skin fibroblast cells in the subject's skin with an effective concentration of a composition containing a partially purified extracellular metabolite preparation from *Bacillus coagulans* MTCC 5856, to bring about the effect of protection against UV-A and UV-B induced cell damage and apoptosis, wherein the partially purified extracellular metabolite preparation is obtained using a process comprising steps of:
   a) inoculating a culture of *Bacillus coagulans* MTCC 5856 into 1.0 liter of Glucose Yeast Extract Acetate broth medium or MRS broth containing 0.5% Tween 80 or Corn steep powder media to initiate bacterial fermentation;
   b) allowing the bacterial fermentation in the inoculated medium of step a) to proceed for 24-48 h at 37° C. with 120 rpm;
   c) centrifuging the fermentation broth of step b) at 4000-7000 rpm and collecting supernatant;
   d) concentrating the supernatant of step c) 10-fold by using a rotary evaporator at 50° C.;
   e) adding 150 ml of chilled acetone drop by drop to 100 ml of the 10-fold concentrated supernatant of step d), followed by mixing to form a supernatant-acetone mixture;
   f) incubating the supernatant-acetone mixture of step e) at 0° C. for 30 minutes followed by centrifuging at 7000-8000 rpm to collect a pellet;
   g) discarding the pellet obtained in step f) and collecting 60% (v/v) acetone-saturated supernatant;
   h) concentrating the acetone-saturated supernatant in step g) 4-fold by rotary evaporator;
   i) adjusting the pH of the supernatant of step h) to 5.0 by using 4N HCl; and
   j) freeze drying the supernatant of step i) to obtain the partially purified extracellular metabolite preparation.

2. The method as in claim 1, wherein the effective concentration of the partially purified extracellular metabolite preparation is in a range of from 0.01% v/v to 2.0% v/v of the total composition.

3. The method as in claim 1, wherein contacting the composition with the skin fibroblast cells in the subject's skin brings about the further effects of reducing oxidative stress in the subject's skin by scavenging ROS, and reducing inflammation by decreasing the levels of inflammatory markers in the subject's skin.

4. The method as in claim 1, wherein the composition further comprises pharmaceutically/cosmetically acceptable excipients, adjuvants, bases, diluents, carriers, conditioning agents, bioavailability enhancers, antioxidants, preservatives, and/or skin care ingredients.

5. The method as in claim 4, wherein the composition is in the form of a cream, a gel, a lotion, a powder, a serum, an oil, a suspension, an ointment, a soap, a scrub, an emulsion, or a compact.

* * * * *